(12) United States Patent
Dracopoulos et al.

(10) Patent No.: US 9,758,679 B2
(45) Date of Patent: *Sep. 12, 2017

(54) MICROBE MITIGATING ARCHITECTURAL BARRIERS, COMPOSITIONS FOR FORMING SUCH BARRIERS AND RELATED METHODS

(71) Applicant: Henry Company LLC, El Segundo, CA (US)

(72) Inventors: John Dracopoulos, Pierrefonds (CA); Lionel Borenstein, Laval (CA); Shawn Melancon, St-Jean-sur-Richelieu (CA)

(73) Assignee: Henry Company, LLC, El Segundo, CA (US)

( * ) Notice: Subject to any disclaimer, the term of this patent is extended or adjusted under 35 U.S.C. 154(b) by 21 days.

This patent is subject to a terminal disclaimer.

(21) Appl. No.: 14/972,656

(22) Filed: Dec. 17, 2015

(65) Prior Publication Data

US 2016/0102211 A1 Apr. 14, 2016

Related U.S. Application Data

(62) Division of application No. 13/028,476, filed on Feb. 16, 2011.

(Continued)

(51) Int. Cl.
| | |
|---|---|
| *C09D 5/14* | (2006.01) |
| *C09D 133/10* | (2006.01) |
| *C09D 133/20* | (2006.01) |
| *C09D 133/26* | (2006.01) |
| *A01N 25/10* | (2006.01) |
| *A01N 25/24* | (2006.01) |
| *A01N 25/34* | (2006.01) |
| *B32B 27/18* | (2006.01) |
| *E04B 1/66* | (2006.01) |
| *C09D 133/08* | (2006.01) |
| *B32B 13/04* | (2006.01) |
| *B32B 7/12* | (2006.01) |

(Continued)

(52) U.S. Cl.
CPC .............. *C09D 5/14* (2013.01); *A01N 25/10* (2013.01); *A01N 25/24* (2013.01); *A01N 25/34* (2013.01); *B32B 7/12* (2013.01); *B32B 9/002* (2013.01); *B32B 9/005* (2013.01); *B32B 9/043* (2013.01); *B32B 11/02* (2013.01); *B32B 11/042* (2013.01); *B32B 11/046* (2013.01); *B32B 11/10* (2013.01); *B32B 13/042* (2013.01); *B32B 21/045* (2013.01); *B32B 25/02* (2013.01); *B32B 25/10* (2013.01); *B32B 25/14* (2013.01); *B32B 27/08* (2013.01); *B32B 27/18* (2013.01); *C09D 133/08* (2013.01); *C09D 133/10* (2013.01); *C09D 133/20* (2013.01); *C09D 133/26* (2013.01); *E04B 1/66* (2013.01); *B32B 2262/062* (2013.01); *B32B 2262/101* (2013.01); *B32B 2264/0207* (2013.01); *B32B 2264/062* (2013.01); *B32B 2264/10* (2013.01); *B32B 2264/102* (2013.01); *B32B 2264/104* (2013.01); *B32B 2264/108* (2013.01); *B32B 2270/00* (2013.01); *B32B 2307/7145* (2013.01); *B32B 2307/724* (2013.01); *B32B 2307/726* (2013.01); *B32B 2307/7242* (2013.01); *B32B 2307/7265* (2013.01); *B32B 2419/04* (2013.01); *B32B 2607/00* (2013.01); *E04B 1/665* (2013.01)

(58) Field of Classification Search
CPC ..................................................... A01N 37/34
See application file for complete search history.

(56) References Cited

U.S. PATENT DOCUMENTS

| | | |
|---|---|---|
| 4,571,415 A | 2/1986 | Jordan |
| 5,283,005 A | 2/1994 | Nelson, Jr. et al. |

(Continued)

FOREIGN PATENT DOCUMENTS

| | | |
|---|---|---|
| DE | 82 793 | 6/1971 |
| EP | 0201167 A1 | 11/1986 |

(Continued)

OTHER PUBLICATIONS

Simpson et al. "Long Term Protection with Fungicide and Algicide Development", PPCJ. Polymers Paint Colour Journal, FMJ International, Redhill, GB, vol. 186, pp. 7-8, Jan. 1, 1996.

*Primary Examiner* — Adam C Milligan
*Assistant Examiner* — Sarah Alawadi
(74) *Attorney, Agent, or Firm* — Baker & Hostetler LLP

(57) ABSTRACT

The invention includes a microbe-mitigating architectural barrier that includes a barrier forming material, and at least one biocide. The barrier forming material may be a bitumen product, an elastomeric polymer and combinations thereof. The microbe-mitigating architectural barrier may be formed by applying an emulsion composition directly to an architectural surface, or may be pre-formed and adhered or otherwise secured to the architectural surface in the form of a sheet or film.

The invention also includes architectural assemblies and/or building envelopes that include the microbe-mitigating barrier. Related methods encompassed within the invention include a method of preparing an architectural barrier that includes: (a) preparing an emulsion that comprises a barrier forming material chosen from a bitumen product, an elastomeric polymer and combinations thereof, and at least one biocide, (b) applying the emulsion to at least one architectural surface, and (c) drying and/and or curing the emulsion to form a barrier.

2 Claims, 2 Drawing Sheets

Related U.S. Application Data

(60) Provisional application No. 61/305,402, filed on Feb. 17, 2010.

(51) Int. Cl.

| | | |
|---|---|---|
| *B32B 9/00* | (2006.01) | |
| *B32B 9/04* | (2006.01) | |
| *B32B 11/02* | (2006.01) | |
| *B32B 11/04* | (2006.01) | |
| *B32B 11/10* | (2006.01) | |
| *B32B 21/04* | (2006.01) | |
| *B32B 25/02* | (2006.01) | |
| *B32B 25/10* | (2006.01) | |
| *B32B 25/14* | (2006.01) | |
| *B32B 27/08* | (2006.01) | |

(56) References Cited

U.S. PATENT DOCUMENTS

| | | |
|---|---|---|
| 5,364,894 A | 11/1994 | Portfolio |
| 5,939,203 A | 8/1999 | Kappock et al. |
| 5,990,043 A | 11/1999 | Kugler et al. |
| 6,245,381 B1 | 6/2001 | Israel |
| 6,492,445 B2 | 12/2002 | Siddiqui et al. |
| 7,641,912 B1 | 1/2010 | Redler |
| 2004/0180195 A1 | 9/2004 | Macuga |
| 2004/0185212 A1 | 9/2004 | Bogrett |
| 2004/0192132 A1 | 9/2004 | Fay et al. |
| 2005/0139126 A1 | 6/2005 | Khan et al. |
| 2005/0170721 A1 | 8/2005 | Toas et al. |
| 2006/0035097 A1* | 2/2006 | Batdorf .................. A01N 25/10 |
| | | 428/507 |
| 2007/0160766 A1 | 7/2007 | Copeland |
| 2007/0294976 A1 | 12/2007 | Fay |

FOREIGN PATENT DOCUMENTS

| | | | |
|---|---|---|---|
| EP | 1798258 A1 | | 6/2007 |
| JP | 08-48917 | | 2/1996 |
| JP | 9-507084 | | 7/1997 |
| JP | 2001-524976 | | 12/2001 |
| JP | 2002-138220 | | 5/2002 |
| JP | 2006-523248 | | 10/2006 |
| JP | 2007-169449 | | 7/2007 |
| JP | 2008-527065 | | 7/2008 |
| JP | 2009-527357 | | 7/2009 |
| WO | WO9112282 | * | 2/1991 |
| WO | WO9943495 | | 9/1999 |
| WO | WO 01/94718 | | 12/2001 |
| WO | WO2004103071 | | 12/2004 |
| WO | WO 2005/061228 | | 7/2005 |
| WO | WO2006127649 | | 11/2006 |

* cited by examiner

Table 1 - Test Formulation

| Composition | Acrylic latex | Aluminum trihydrate/polymer | Foamaster NXZ | Modified hydroxyethylcellulose (Natrosol Powder) | Cellulose | Plasticizer (Santicizer 160) | Bentonite | Calcium Carbonate | Iron Oxide (Black) | Titanium dioxide | TEXIPOL | TAMOL | BYK 031 | Triton CF10 | SUNDEX780/RAFFEX | preservative | ethylene glycol | butyl carbitol/glycol ether | KOH (45% solution) | Potassium tripoly phosphate | ammonia hydroxide (20% solution) | Water | Omadine | Irgasan P-20T | Nuocide |
|---|---|---|---|---|---|---|---|---|---|---|---|---|---|---|---|---|---|---|---|---|---|---|---|---|---|
| 1 | 38.0 | 38.0 | 0.29 | 0.29 | 1.4 | 2.0 | 1.04 | 1.1 | 5.0 | 1.7 | 0 | 0.34 | 0 | 0 | 0 | 0.2 | 2.2 | 2.5 | 0 | 0.07 | 0 | 8.7 | 0 | 0 | 0 |
| 2 | 38.0 | 38.0 | 0.29 | 0.29 | 1.4 | 2.0 | 1.04 | 1.1 | 5.0 | 1.7 | 0 | 0.34 | 0 | 0 | 0 | 0.2 | 2.2 | 2.5 | 0 | 0.07 | 0 | 8.7 | 1 | 0 | 0 |
| 3 | 38.0 | 38.0 | 0.29 | 0.29 | 1.4 | 2.0 | 1.04 | 1.1 | 5.0 | 1.7 | 0 | 0.34 | 0 | 0 | 0 | 0.2 | 2.2 | 2.5 | 0 | 0.07 | 0 | 8.7 | 0.2 | 0 | 0 |
| 4 | 38.0 | 38.0 | 0.29 | 0.29 | 1.4 | 2.0 | 1.04 | 1.1 | 5.0 | 1.7 | 0 | 0.34 | 0 | 0 | 0 | 0.2 | 2.2 | 2.5 | 0 | 0.07 | 0 | 8.7 | 0.02 | 0 | 0 |
| 5 | 38.0 | 38.0 | 0.29 | 0.29 | 1.4 | 2.0 | 1.04 | 1.1 | 5.0 | 1.7 | 0 | 0.34 | 0 | 0 | 0 | 0.2 | 2.2 | 2.5 | 0 | 0.07 | 0 | 8.7 | 0 | 1 | 0 |
| 6 | 38.0 | 38.0 | 0.29 | 0.29 | 1.4 | 2.0 | 1.04 | 1.1 | 5.0 | 1.7 | 0 | 0.34 | 0 | 0 | 0 | 0.2 | 2.2 | 2.5 | 0 | 0.07 | 0 | 8.7 | 0 | 0.2 | 0 |
| 7 | 38.0 | 38.0 | 0.29 | 0.29 | 1.4 | 2.0 | 1.04 | 1.1 | 5.0 | 1.7 | 0 | 0.34 | 0 | 0 | 0 | 0.2 | 2.2 | 2.5 | 0 | 0.07 | 0 | 8.7 | 0 | 0.02 | 0 |
| 8 | 38.0 | 38.0 | 0.29 | 0.29 | 1.4 | 2.0 | 1.04 | 1.1 | 5.0 | 1.7 | 0 | 0.34 | 0 | 0 | 0 | 0.2 | 2.2 | 2.5 | 0 | 0.07 | 0 | 8.7 | 0 | 0 | 1 |
| 9 | 38.0 | 38.0 | 0.29 | 0.29 | 1.4 | 2.0 | 1.04 | 1.1 | 5.0 | 1.7 | 0 | 0.34 | 0 | 0 | 0 | 0.2 | 2.2 | 2.5 | 0 | 0.07 | 0 | 8.7 | 0 | 0 | 0.2 |
| 10 | 38.0 | 38.0 | 0.29 | 0.29 | 1.4 | 2.0 | 1.04 | 1.1 | 5.0 | 1.7 | 0 | 0.34 | 0 | 0 | 0 | 0.2 | 2.2 | 2.5 | 0 | 0.07 | 0 | 8.7 | 0 | 0 | 2 |
| 11 | 38.5 | 0 | 0.3 | 0.3 | 1.4 | 3.0 | 1.04 | 1.1 | 5.0 | 1.7 | 0.9 | 0.3 | 0.3 | 0.23 | 9.4 | 0.12 | 0 | 0 | 0 | 0.07 | 0 | 8.7 | 0 | 0 | 0 |
| 12 | 38.5 | 0 | 0.3 | 0.3 | 1.4 | 3.0 | 1.04 | 1.1 | 5.0 | 1.7 | 0.9 | 0.3 | 0.3 | 0.23 | 9.4 | 0.12 | 0 | 0 | 0 | 0.07 | 0 | 8.7 | 1 | 0 | 0 |
| 13 | 38.5 | 0 | 0.3 | 0.3 | 1.4 | 3.0 | 1.04 | 1.1 | 5.0 | 1.7 | 0.9 | 0.3 | 0.3 | 0.23 | 9.4 | 0.12 | 0 | 0 | 0 | 0.07 | 0 | 8.7 | 0.2 | 0 | 0 |
| 14 | 38.5 | 0 | 0.3 | 0.3 | 1.4 | 3.0 | 1.04 | 1.1 | 5.0 | 1.7 | 0.9 | 0.3 | 0.3 | 0.23 | 9.4 | 0.12 | 0 | 0 | 0 | 0.07 | 0 | 8.7 | 0.02 | 0 | 0 |
| 15 | 38.5 | 0 | 0.3 | 0.3 | 1.4 | 3.0 | 1.04 | 1.1 | 5.0 | 1.7 | 0.9 | 0.3 | 0.3 | 0.23 | 9.4 | 0.12 | 0 | 0 | 0 | 0.07 | 0 | 8.7 | 0 | 1 | 0 |
| 16 | 38.5 | 0 | 0.3 | 0.3 | 1.4 | 3.0 | 1.04 | 1.1 | 5.0 | 1.7 | 0.9 | 0.3 | 0.3 | 0.23 | 9.4 | 0.12 | 0 | 0 | 0 | 0.07 | 0 | 8.7 | 0 | 0.2 | 0 |
| 17 | 38.5 | 0 | 0.3 | 0.3 | 1.4 | 3.0 | 1.04 | 1.1 | 5.0 | 1.7 | 0.9 | 0.3 | 0.3 | 0.23 | 9.4 | 0.12 | 0 | 0 | 0 | 0.07 | 0 | 8.7 | 0 | 0.02 | 0 |
| 18 | 38.5 | 0 | 0.3 | 0.3 | 1.4 | 3.0 | 1.04 | 1.1 | 5.0 | 1.7 | 0.9 | 0.3 | 0.3 | 0.23 | 9.4 | 0.12 | 0 | 0 | 0 | 0.07 | 0 | 8.7 | 0 | 0 | 1 |
| 19 | 38.5 | 0 | 0.3 | 0.3 | 1.4 | 3.0 | 1.04 | 1.1 | 5.0 | 1.7 | 0.9 | 0.3 | 0.3 | 0.23 | 9.4 | 0.12 | 0 | 0 | 0 | 0.07 | 0 | 8.7 | 0 | 0 | 0.2 |
| 20 | 38.5 | 0 | 0.3 | 0.3 | 1.4 | 3.0 | 1.04 | 1.1 | 5.0 | 1.7 | 0.9 | 0.3 | 0.3 | 0.23 | 9.4 | 0.12 | 0 | 0 | 0 | 0.07 | 0 | 8.7 | 0 | 0 | 2 |
| 21 | 45.0 | 0 | 0.2 | 0 | 0 | 0 | 0 | 33.0 | 0.25 | 1.0 | 2.0 | 0.3 | 0 | 0 | 0 | 0.2 | 0 | 0 | 0.3 | 0 | 0.25 | 17.5 | 0 | 0 | 0 |
| 22 | 45.0 | 0 | 0.2 | 0 | 0 | 0 | 0 | 33.0 | 0.25 | 1.0 | 2.0 | 0.3 | 0 | 0 | 0 | 0.2 | 0 | 0 | 0.3 | 0 | 0.25 | 17.5 | 1 | 0 | 0 |
| 23 | 45.0 | 0 | 0.2 | 0 | 0 | 0 | 0 | 33.0 | 0.25 | 1.0 | 2.0 | 0.3 | 0 | 0 | 0 | 0.2 | 0 | 0 | 0.3 | 0 | 0.25 | 17.5 | 0.2 | 0 | 0 |
| 24 | 45.0 | 0 | 0.2 | 0 | 0 | 0 | 0 | 33.0 | 0.25 | 1.0 | 2.0 | 0.3 | 0 | 0 | 0 | 0.2 | 0 | 0 | 0.3 | 0 | 0.25 | 17.5 | 0.02 | 0 | 0 |
| 25 | 45.0 | 0 | 0.2 | 0 | 0 | 0 | 0 | 33.0 | 0.25 | 1.0 | 2.0 | 0.3 | 0 | 0 | 0 | 0.2 | 0 | 0 | 0.3 | 0 | 0.25 | 17.5 | 0 | 1 | 0 |
| 26 | 45.0 | 0 | 0.2 | 0 | 0 | 0 | 0 | 33.0 | 0.25 | 1.0 | 2.0 | 0.3 | 0 | 0 | 0 | 0.2 | 0 | 0 | 0.3 | 0 | 0.25 | 17.5 | 0 | 0.2 | 0 |
| 27 | 45.0 | 0 | 0.2 | 0 | 0 | 0 | 0 | 33.0 | 0.25 | 1.0 | 2.0 | 0.3 | 0 | 0 | 0 | 0.2 | 0 | 0 | 0.3 | 0 | 0.25 | 17.5 | 0 | 0.02 | 0 |
| 28 | 45.0 | 0 | 0.2 | 0 | 0 | 0 | 0 | 33.0 | 0.25 | 1.0 | 2.0 | 0.3 | 0 | 0 | 0 | 0.2 | 0 | 0 | 0.3 | 0 | 0.25 | 17.5 | 0 | 0 | 1 |
| 29 | 45.0 | 0 | 0.2 | 0 | 0 | 0 | 0 | 33.0 | 0.25 | 1.0 | 2.0 | 0.3 | 0 | 0 | 0 | 0.2 | 0 | 0 | 0.3 | 0 | 0.25 | 17.5 | 0 | 0 | 0.2 |
| 30 | 45.0 | 0 | 0.2 | 0 | 0 | 0 | 0 | 33.0 | 0.25 | 1.0 | 2.0 | 0.3 | 0 | 0 | 0 | 0.2 | 0 | 0 | 0.3 | 0 | 0.25 | 17.5 | 0 | 0 | 2 |

Fig. 1

Table 2

| Composition | A. niger (Average of 3) | P. cirrinum (Average of 3) | A. pullalans (Average of 3) |
|---|---|---|---|
| 1 | 0 | 0 | 0 |
| 2 | 9 | 9 | 9 |
| 3 | 7 | 7 | 7 |
| 4 | 6 | 6 | 6 |
| 5 | 9 | 9 | 9 |
| 6 | 6 | 6 | 5 |
| 7 | 8 | 9 | 8 |
| 8 | 9 | 9 | 9 |
| 9 | 5 | 5 | 4 |
| 10 | 1 | 1 | 2 |
| 11 | 1 | 1 | 1 |
| 12 | 9 | 9 | 9 |
| 13 | 8 | 9 | 9 |
| 14 | 8 | 7 | 7 |
| 15 | 9 | 8 | 9 |
| 16 | 6 | 6 | 7 |
| 17 | 7 | 7 | 7 |
| 18 | 9 | 9 | 9 |
| 19 | 8 | 9 | 9 |
| 20 | 9 | 9 | 9 |
| 21 | 0 | 1 | 0 |
| 22 | 9 | 9 | 9 |
| 23 | 3 | 4 | 3 |
| 24 | 7 | 7 | 6 |
| 25 | 6 | 7 | 7 |
| 26 | 8 | 8 | 9 |
| 27 | 7 | 8 | 8 |
| 28 | 9 | 9 | 9 |
| 29 | 3 | 3 | 3 |
| 30 | 2 | 2 | 2 |

Fig. 2

MICROBE MITIGATING ARCHITECTURAL BARRIERS, COMPOSITIONS FOR FORMING SUCH BARRIERS AND RELATED METHODS

CROSS REFERENCE TO RELATED APPLICATIONS

This application is a Divisional application of U.S. Non-provisional patent application Ser. No. 13/028,476, filed Feb. 16, 2011, which claims the benefit of U.S. Provisional Patent Application No. 61/305,402, filed Feb. 17, 2010, which are hereby incorporated by reference in their entirety.

BACKGROUND

Often the walls or architectural elements of a building are exposed to moisture. Moisture and water or water vapor can collect on surfaces. Such moisture has several origins, such as, for example, water vapor diffusion and air leakage from the interior or exterior. Trapped or collected moisture within walls or other elements may bring adverse effects, including corrosion of the element or nearby structures, erosion of structural integrity and/or growth of mold or other microbes. The building industry has recognized that one means of reducing moisture collection is to control air leakage, i.e., to control the movement of air and water vapor through the building envelope. Under ordinary circumstances, the movement of air into a building (infiltration) and out of a building (exfiltration) may be caused by pressure differences produced by wind, stack or chimney effect and fan pressurization. Air leakage may follow such paths as holes or openings through the envelope, for example, cracks or joints between infill components and structural elements or through porous materials such as concrete block and porous insulation materials. Various formulations for barrier and films that serve to control air flow have been developed and have helped to reduce the moisture collection and associated problems to some degree.

Nonetheless, growth of mold and other microbes remains a problem, especially in humid geographies. However, no conventional architectural barriers have been formulated to address this problem. Thus, there remains a need in the art for an architectural barrier that functions to control air flow and simultaneously to reduce the growth of mold and/or other microbes.

SUMMARY

The invention includes a microbe-mitigating architectural barrier that includes a barrier forming material, and at least one biocide. The barrier forming material may be a bitumen product, an elastomeric polymer and combinations thereof. The microbe-mitigating architectural barrier may be formed by applying an emulsion composition directly to an architectural surface, or it may be pre-formed and adhered or otherwise secured to the architectural surface in the form of a sheet or film.

The invention also includes architectural assemblies and/or building envelopes that include the microbe-mitigating barrier. Related methods are encompassed within the scope of the invention. Such methods include a method of preparing an architectural barrier that includes: (a) preparing an emulsion that comprises a barrier forming material chosen from a bitumen product, an elastomeric polymer and combinations thereof, and at least one biocide, (b) applying the emulsion to at least one architectural surface, and (c) drying and/and or curing the emulsion to form a barrier.

Also included are methods of preparing an architectural assembly that includes an architectural element coated with the barrier of the invention.

The invention further provides an emulsion for use in the preparation of a microbe mitigating architectural barrier including water, a barrier forming material, and at least one biocide. In the emulsion, the barrier forming material may be a bitumen product, an elastomeric polymer and combinations thereof.

BRIEF DESCRIPTION OF THE SEVERAL VIEWS OF THE DRAWINGS

The foregoing summary as well as the following detailed description of the invention, may be better understood when read in conjunction with the appended drawings. It should be understood that the invention is not limited to the precise arrangements and instrumentalities shown. In the drawings:

FIG. 1 is a Table of showing each of the compositions of Compositions 1-30 which were evaluated as described in Example 1; and FIG. 2 is a Table showing data collected in the evaluation tests of the Compositions 1-30 shown in FIG. 1.

DETAILED DESCRIPTION OF THE INVENTION

The invention described herein includes architectural air barriers formulated to mitigate and/or substantially prevent microbe growth on or within an architectural structure, such as a wallboard, wall, joist or other structure. The invention also includes building envelopes and building assemblies that include the air barrier described herein, methods of preparing and using such barriers, and the emulsions that are used to prepare the barriers.

By "microbe mitigating", it is meant that the emulsion and/or air barrier reduces a microbe population by direct cidal action, by substantial arrest of cell division or cellular respiration and/or any other mechanism of action; reduces the rate of proliferation of a microbe population; and/or substantially prevents the establishment of a microbe population on a surface to which the barrier or emulsion is applied; as compared to the same activity(ies) or a surface that does not bear the emulsion or barrier of the invention.

By "microbe" it is meant any of one or more prokaryotic or eukaryotic single or multi-celled organisms, including, for example, bacteria, molds, lichens, algaes, organisms of kingdom fungi (including yeasts), organisms conventionally regarded as protists, organisms of the kingdom formerly know as Monera, viruses, and amoebae.

By "effective amount," it is meant an amount sufficient to prevent, eliminate, and/or reduce growth of a microbe population on a surface.

The barriers and emulsions of the invention include a barrier forming material. Any material that can be applied to a surface a form a barrier (permeable or impermeable, continuous or discontinuous) may be used. It may be preferred that the barrier forming material is a polymer (such term, when used herein, including both polymer of homogenous monomers and heterogeneous monomers (the latter often referred to as "copolymer"), bitumen products, polymer modified bitumens (e.g., bitumens into which polymers are dispersed and reside within the bitumen matrix), and/or combinations of both.

If the selected barrier forming material includes a polymer, such polymers may be any known or developed in the art. Suitable examples may include any elastomeric polymers. Other examples include polymers and/or copolymers of acrylates, methacrylates, acrylonitrile, acrylamides, methacrylamides, styrene-butadiene-styrene and mixtures thereof. In some embodiments, it may be preferred that polymer contains at least one functional group, such as, without limitation a vinyl group, a styrene group and/or urethane, olefin, hydroxyl, carboxyl, and acrylic.

Bitumen products may include, for example, asphalt, tars, polymer modified bitumen and mixtures of the same. If an asphalt is included in the barrier or emulsion of the invention, it may be preferred that the asphalt has a penetration grade ("pen grade") at 25° C., when tested according to ASTM method D 5, of about 0.5 to about 30, alternatively about 1 to about 20, or about 3 to about 15 (all at 25° C.). Similarly, it may be desirable that the selected asphalt has a softening point of about 62° C. to about 95° C.

Suitable polymer-modified bitumens may include, without limitation SBS-modified bitumens, and other polymer-modified bitumens, such as those modified by SIS, SEBS, SP and PB.

The emulsions and/or barriers of the invention additionally contain at least one biocide. Such biocide may be any known or developed in the art and may accomplish its cidal activity through any mechanical and/or cellular mechanism. For example, the selected biocide may mechanically or biochemically disrupt the cellular membrane or protein coating of the microbe, thereby killing it or restricting its ability to reproduce. Alternatively, the biocide(s) selected may inhibit the cellular respiration of one or more of the target microbes.

Exemplary biocides may include, without limitation silver-containing materials, gold-containing materials, aluminum-containing materials, copper-containing materials, fungicides, antimycotics, bactericides, viricides, carbamates, triclosan, or mixtures of the same. Commercially available fungicides include the POLYPHASE® series from Troy Chemical Corporation, Newark, N.J.; and the NUOCIDE® series available from International Specialty Products, Cranbury, N.J.

Depending on the end use of the barrier and/or emulsion, the specific biocide used may be targeted to the organisms that are likely to be encountered in the end use environment. For example, if the barrier is to be used as an architectural barrier or in part of a building envelope in a residentially or commercial building, the selected biocide(s) may include a fungicide or other antimycotic. If the barrier is to be used in a building that houses a food processing or storage facility or medical facility, the selected biocide(s) may include bactericides and/or viricides.

Regardless of the specific barrier forming material(s) and biocide(s) used in a given barrier or emulsions, the biocide should be present in the emulsion in an amount sufficient to exhibit a level of microbe mitigating activity when such emulsion is formed into an air barrier. As appreciated by one of ordinary skill in the art, such amount will necessarily be variable depending on numerous factors, such as the nature and number of other components present in the emulsion, the specific biocide(s) used, and the level of microbe mitigating activity desired in the end product.

However, in some circumstances, it may be desirable that the weight ratio of the barrier forming material(s) to the biocide(s) in the barrier is about 30 parts to about 1 part, about 40 parts to about 1 part, about 50 parts to about 1 part, about 60 parts to about 1 part, about 70 parts to about 1 part, about 80 parts to about 1 part, by weight. In some embodiments, it may be preferred that the ratio is from about 1:about 200 to about 1:about 2.

The barrier and or emulsion may include one or more additional additives. Additives may include water, other solvents, crumb rubber, latex, calcium carbonate, carbon black, bentonite, laponite, clay, quartz, silica, titanium dioxide, cellulose, and mixtures thereof. Other exemplary additives may include a flame retardant, adhesives, a colorant, a pigment, an odorant, petroleum distillates, styrene-butadiene-styrene (or other polymers), organotitantes, waxes, stabilizers, organic titanium compounds, organic zirconium compounds, and rheology modifiers.

Also included within the scope of the invention are building envelopes that include the microbe-mitigating barrier of the invention. Such envelopes can include those for residential structures, commercial structures, industrial structures and the like.

Architectural assemblies that include at least one architectural element that is coated with the microbe-mitigating barrier of the invention are also included. Architectural elements can include, without limitation, wallboard (inner and/or outer surfaces), stone, cement, frame wood structures, bricks or slabs, fiberglass, insulation, oriented strand boards, sheet rock, composite board, plywood, wood, tile, polymer sheets or films, doors, glass and ceramics.

An emulsion for use in the preparation of a microbe mitigating architectural barrier may include water (or other carrier), a barrier forming material as described above, and at least one biocide. Other additives, as described above, may be included. These emulsions may be prepared by any means known in the art and include incorporating the desired amounts of barrier forming material(s), biocide(s), a carrier (such as water) and, optionally, any other components together by agitation or mixing.

The above described barriers, assemblies and envelopes may be prepared by various procedures. For example, a barrier may be prepared by mixing an emulsion that comprises a barrier forming material and at least one biocide, as described above. The emulsion is applied to at least one architectural surface and permitted to dry or cure to form a barrier. Such application may be accomplished by any mechanism, including spraying; wiping; painting; blotting; and/or dip; brushing, immersion; or float coating. For example, the emulsion may be dried to form a barrier under ambient conditions or may be dried under heat (e.g., 30° C. or greater) and/or by application of air current (fanning or blowing). Architectural surfaces include any surface of any architectural element used in the fabrication of a building or structure (including exterior and interior elements), such as, for example, surfaces of wallboard, struts, fames, doors, window frames, stone or concrete blocks, wood, pipes, tubing, fiberboard, composite board, and the like.

Alternatively, the barrier may be prepared by applying (as described above) the emulsion to a detachable base substrate. Such substrate may be any material from which the barrier, once cured or dried may be detached, either mechanically or chemically. Examples of such substrates include for example, plates, rolls, foils, sheets, or slabs of fiberglass, wood, composite, stone, metal or paper. Optionally, the substrate may bear a pattern (such that the barrier prepared bears an embossed design, such as the manufacturer's trademark) and/or pre-coated with a material that facilitates detachment. Such mater33ials may include, for example, oils, solvents, waxes, and non-stick polymers.

In another embodiment, the emulsion is prepared to have sufficient rhelogical properties such that the barrier sheets may be formed by rolling portions of the emulsion material into sheets and/or extruding the emulsion material into sheet, strip, or film.

Once the barrier sheet or film is prepared, it may be applied to the architectural surface by any means. For example, it may be staple, glued, heat or energy fused, tacked, and/or nailed. If desired, an adhesive layer may be applied to at least one surface of the barrier sheet or film prior to application, so that the barrier is self-adhering.

EXAMPLE I

Compositions of the invention were evaluated to test the barriers' ability to resist and/or ameliorate growth of three types of fungi:
(1) *Aspergillus niger;*
(2) *Penicillium citrinum;* and
(3) *Averobasidium pullulans.*

The evaluation was preformed using ASTM D3273 (2000) "Standard Test Method for the Resistance to Growth of Mold on the Surface of Interior Coatings In an Environmental Chamber," §§7.1 to 7.3, attached hereto and the contents of which are incorporated hereby by reference. Panels measuring approximately 3"×4" were prepared by brush coating Compositions 1-30 having the components shown in Table I.

As can be seen from Table I (shown in FIG. 1), three types of biocide were tested at 3 load levels:
(i) Zinc Omadine®, a GRAS zinc complex of pyrithione, available from ARCH Chemicals, Inc. Norwalk, Conn. USA;
(ii) TROYSAR® p-20t, a carbamate fungicide available from Troy Corporation, Florham Park, N.J., USA;
(iii) Nuocide®, a form of tetrachloroisophthalonitrile, available from ISP, Cranbury N.J., USA.

Positive control specimen panels were prepared by inoculating the panels surfaces with (1) $1.0 \times 10^5$ cfu/ml, *Aspergillus niger*, (2) $1.0 \times 10^5$ cfu/ml Penicllium *citrinum*, or (3) $1.0 \times 10^5$ cfu/ml, *Averobasidium pullulans.*

Mold spores were prepared on slants using 25% non-ionic surfactant. Spores were broken up and placed in solution. The solution was poured over the soil and the mold was permitted to grow for two weeks. Controls were taken to verify the mold growth.

Specimen panels were brought to condition at 23° C.+/−2° C. with 50%+/−5% relative humidity for four days prior to testing. Specimen panels were hung above the soil mixtures containing the mold spores. The positive and negative specimens were also hung in the chamber. Specimen panels and controls were hung for 4 weeks and were periodically checked for growth during the incubation period.

After 4 weeks, a growth rating scale of 0-10 based on ASTM D3273 is taken. "0" indicated complete mold coverage; "10" indicates substantially no visible growth. The results are shown in Table 2 (FIG. 2).

What is claimed:
1. An aqueous emulsion consisting of:
   (a) water in an amount of about 50% by weight or less;
   (b) about 20-90% by weight of an acrylate polymer; and
   (c) one biocide, in an amount of about 0.01-1% selected from the group consisting of carbamate and tetrachloroisophthalonitrile.
2. A substrate coated with a layer of the composition of claim 1.

* * * * *